May 22, 1973 H. B. LEWIS ET AL Plant Pat. 3,338
AZALEA PLANT
Filed Dec. 11, 1970
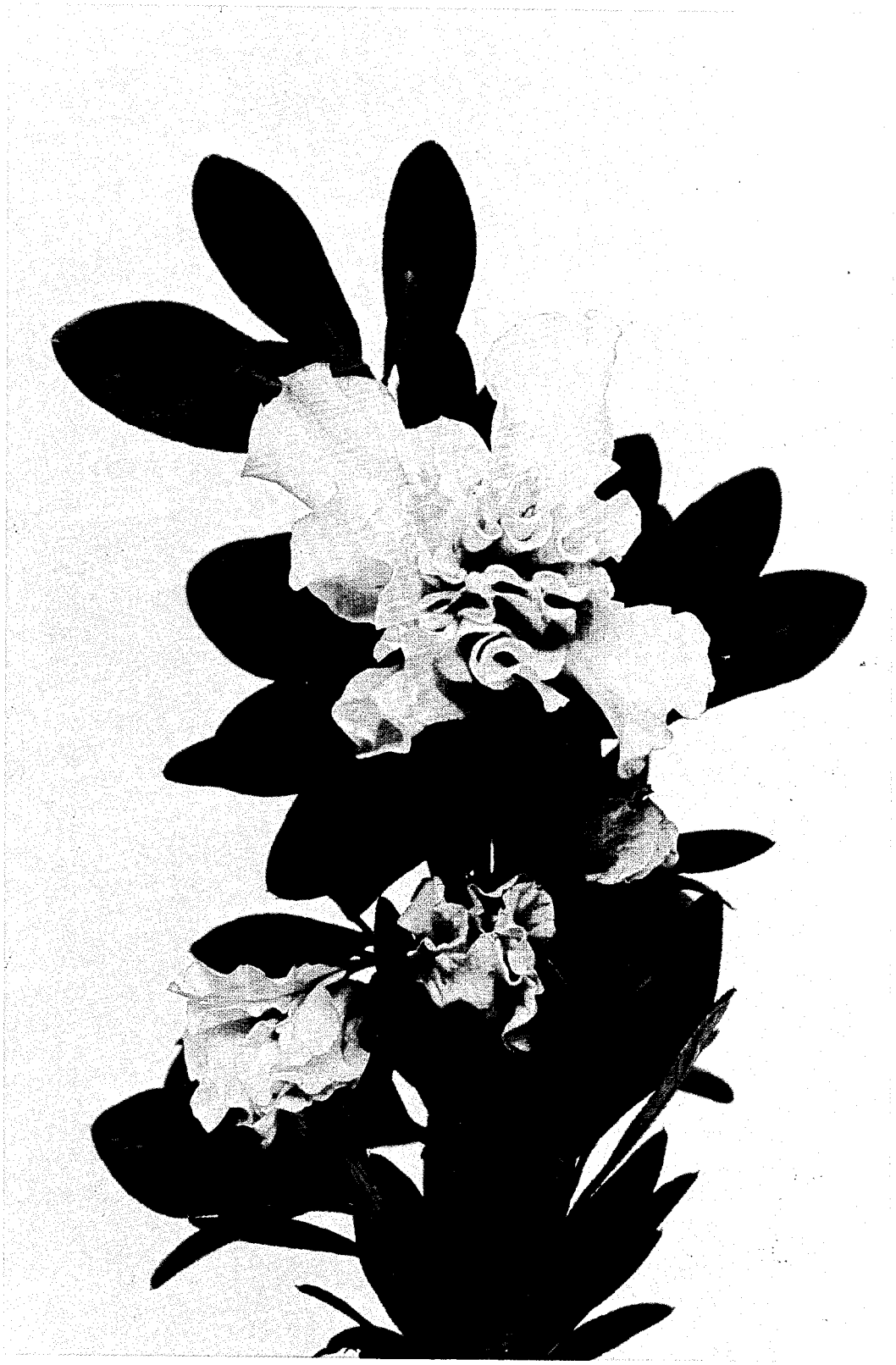

United States Patent Office

Plant Pat. 3,338
Patented May 22, 1973

3,338
AZALEA PLANT

Hubert B. Lewis and Helen H. Lewis, both of 16562 E. Leffingwell Road, Whittier, Calif. 90603

Filed Dec. 11, 1970, Ser. No. 97,399
Int. Cl. A01h 5/00
U.S. Cl. Plt.—56 1 Claim The present invention relates to a new and distinct variety of azalea plant which was originated by us by crossing the azalea variety known as "Pink Pearl" (unpatented) with the azalea variety known as "Pink Perfection" (unpatented), the former being the seed parent and the latter being the pollen parent.

As the result of this breeding, we have produced a new and improved azalea variety which is distinguished from its parents, as well as from all other azalea varieties of which we are aware, as evidenced by the following unique combination of characteristics which are outstanding in the new variety:

(1) A superior habit of growth;
(2) Good flower size;
(3) A flower form very similar to the flowers of the azalea variety known as "Pink Enchantress" (Plant Patent No. 2,310);
(4) A distinctive, attractive and bright Phlox Pink basic flower color with shadings ranging from a pale blush to white and
(5) Excellent suitability for year around forcing.

Asexual reproduction of our new variety by cuttings, as performed by us at Whittier, Calif., shows that the foregoing characteristics and distinctions come true to form and are established and transmitted through succeeding propagations.

The accompanying drawing shows typical specimens of the flowers and foliage of our new azalea variety as depicted in color as nearly true as it is reasonably possible to make the same in a color illustration of this character.

The following is a detailed description of our new variety, with color terminology in accordance with the Horticultural Colour Chart issued by Wilson Colour Ltd. in collaboration with The Royal Horticultural Society, except where general color terms of ordinary dictionary significance are obvious:

Breeding: Seedling.
*Seed parent.*—"Pink Pearl."
*Pollen parent.*—"Pink perfection."
Propagation: Holds its distinguishing characteristics through succeeding propagations by cuttings.
Locality where grown and observed: Whittier, Calif.

*Plant*

Form: Bush; much-branched.
Habit: Vigorous; upright.
Rooting: Very uniform; strong; vigorous.
Blooming habit: Very heavy; in clusters.
Blooming season: Normally in spring, but excellent for year around forcing.
Foliage:
*Size.*—Medium.

*Quantity.*—Normal.
*Color.*—New foliage—upper side—Scheele's Green, Plate 860, page 175; under side—Scheele's green, Plate 860/2, page 175. Old foliage—upper side—Spinach Green, Plate 0960, page 187; under side—Spinach Green, Plate 0960/3, page 187.
*Shape.*—Oval pointed.
*Texture.*—Upper side—glossy. Under side—rough.
*Margin.*—Smooth.
*Aspect.*—Good.
*Disease resistance.*—Normal, as determined by comparison with other azalea varieties grown under the same cultural conditions at Whittier, Calif.

*Flowers*

Borne: From 2 to several to stem; in clusters; on strong stems.
Quantity of bloom: Abundant, both outdoors and in greenhouse.
Continuity: From one season to intermittent.
Size: From 3 inches to 3½ inches in diameter.
Petalage:
*Number of petals under normal conditions.*—Two rows of 5 petals around tufted center.
*Color.*—Basically near Phlox Pink, Plate 625/2, page 77, with darker spots of Phlox Pink, Plate 625/1 on inside of upper petals, and with some shadings ranging from a pale blush to white.
*Texture.*—Firm.
*Appearance.*—Very neat.
*Shape.*—Semi-double hose-in-hose.
*Arrangement.*—Two rows of petals, one offsetting the other, with tuft of small petals in center.

*Reproductive organs*

Stamens: Mostly attached to petals. Color—Yellow tips.
Pollen: Color—White.
Styles: Color—White.
Stigma: Color—Yellow.
Ovaries: Color—Green.
General observations: The flowers of our new variety are very similar in form to those of the variety "Pink Enchantress" (Plant Patent No. 2,310), but our new variety is a much better grower, has somewhat brighter flowers, and is much better adapted to forcing.

We claim:

1. A new and distinct variety of azalea plant, substantially as herein shown and described, characterized particularly as to novelty by the unique combination of a superior habit of growth, good flower size, a flower form very similar to the flowers of the azalea variety known as "Pink Enchantress" (Plant Patent No. 2,310), a distinctive, attractive and bright Phlox Pink basic flower color with shadings ranging from a pale blush to white, and excellent suitability for year around forcing.

No references cited.

ROBERT E. BAGWILL, Primary Examiner